United States Patent [19]

Severino

[11] 4,172,099

[45] Oct. 23, 1979

[54] PROCESS FOR CHLORINATION OF ETHYLENE

[75] Inventor: Frank T. Severino, Teaneck, N.J.

[73] Assignee: Stauffer Chemical Company, Westport, Conn.

[21] Appl. No.: 581,071

[22] Filed: May 27, 1975

Related U.S. Application Data

[63] Continuation of Ser. No. 481,584, Jun. 26, 1974, abandoned, which is a continuation of Ser. No. 257,494, May 30, 1972, abandoned.

[51] Int. Cl.² ............................................. C07C 17/02
[52] U.S. Cl. ............................. 260/660; 260/652 P; 260/654 H; 260/656 R; 260/658 R; 260/659 A
[58] Field of Search ............... 260/660, 659 A, 656 R, 260/652 P

[56] References Cited

U.S. PATENT DOCUMENTS

| | | | |
|---|---|---|---|
| 2,929,852 | 3/1960 | Benedict | 260/260 |
| 3,378,597 | 4/1968 | Dehn et al. | 260/659 A |
| 3,548,014 | 12/1970 | Jacobowsky et al. | 260/656 R |
| 3,839,475 | 10/1974 | Kurtz et al. | 260/660 |
| 3,923,913 | 12/1975 | Antonini et al. | 260/660 X |

FOREIGN PATENT DOCUMENTS

| | | | |
|---|---|---|---|
| 1959211 | 6/1970 | Fed. Rep. of Germany | 260/656 R |
| 603809 | 6/1948 | United Kingdom | 260/656 R |
| 1231127 | 5/1971 | United Kingdom | 260/660 |

*Primary Examiner*—Robert V. Hines
*Attorney, Agent, or Firm*—Michael J. Bradley

[57] ABSTRACT

Process for the chlorination of ethylene in which the excess heat of reaction from the chlorination is utilized for fractionation of the reaction product and another dichloroethane containing stream, and in which an impure, neutralized, and dried ethylene dichloride-containing oxychlorination effluent is supplied to the liquid reaction medium in which the chlorination of the ethylene is conducted.

4 Claims, 1 Drawing Figure

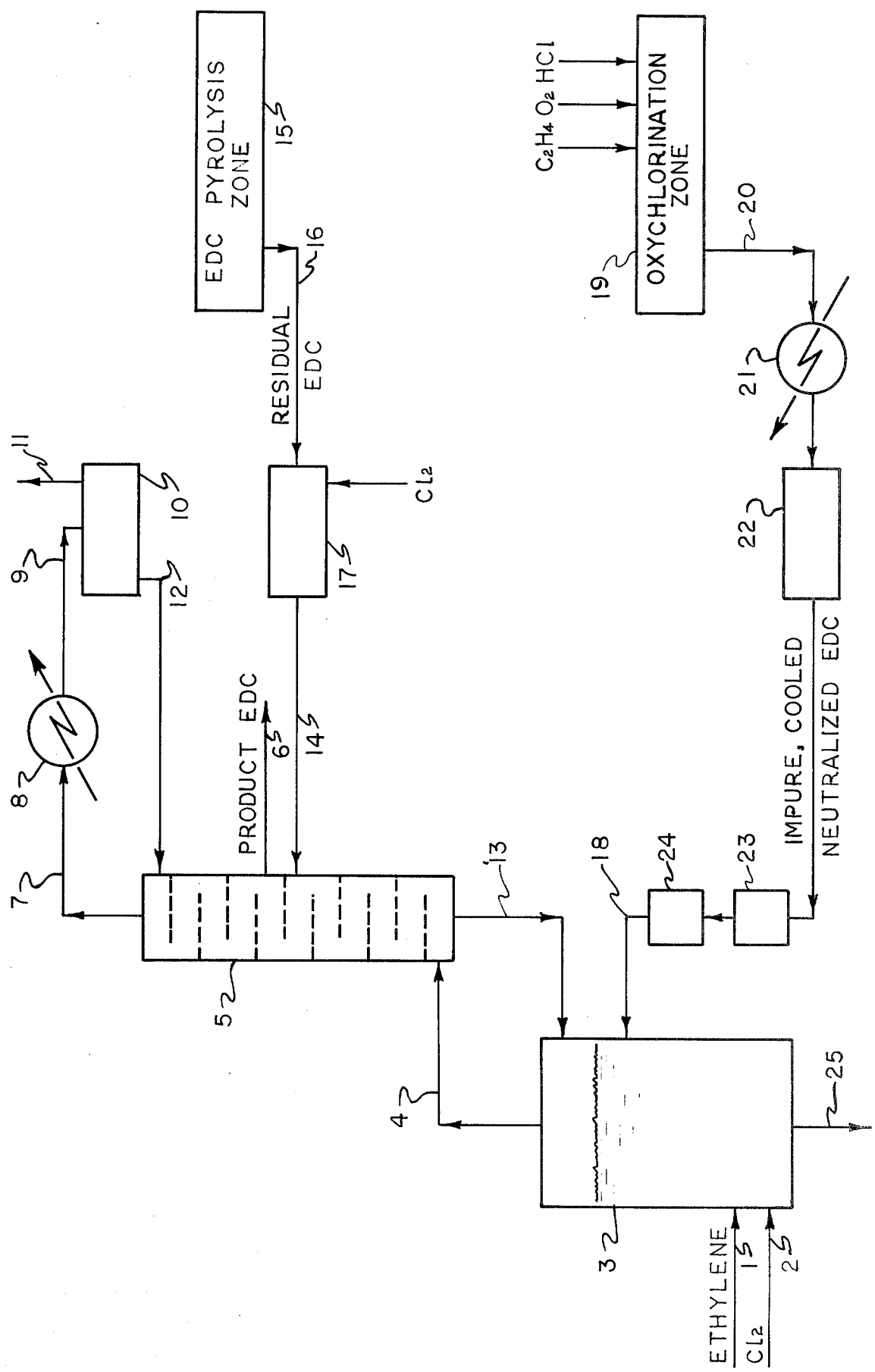

PROCESS FOR CHLORINATION OF ETHYLENE

This is a continuation, of application Ser. No. 481,584 filed June 26, 1974 which is a continuation of application Ser. No. 257,494 filed May 30, 1972, both now abandoned.

BACKGROUND OF THE INVENTION

The present invention relates to the preparation of ethylene dichloride, and in particular to the addition chlorination of ethylene. In its preferred form, the invention relates to a novel process for preparing 1,2-dichloroethane by addition chlorination, wherein the heat generated by the reaction of chlorine and ethylene is used to vaporize and rectify the ethylene dichloride produced, and is also used to vaporize and rectify crude ethylene dichloride from other sources.

The preparation of dichloroalkanes by the chlorination of an appropriate olefin in the liquid phase under suitable conditions is well known. British Pat. No. 1,231,127 discloses a method of preparing dichloroalkanes wherein an olefin is addition chlorinated (with chlorine) in the liquid phase at suitable temperatures, whereby the dichloroalkane formed is distilled or vaporized, and is passed to a closely related distillation column which is also fed with crude dichloroalkane obtained from at least one other source. The heat of reaction contained in the vaporized dichloroalkane is used to rectify the dichloroalkane vapor, and because of the large excess of heat present, is used additionally to rectify the crude dichloroalkane from another source, e.g., crude dichloroalkane obtained from the oxychlorination of an olefin, and/or unconverted recycle dichloroalkane from a pyrolysis system in which dichloroalkane is pyrolyzed to a given monochloroalkene.

This procedure has a number of disadvantages. To begin with, severe problems arise from the introduction of an ethylene oxychlorination effluent directly into the fractionation column, as described in the patent. For example, water present in oxychlorination effluents, unless removed prior to fractionation, will provide severe corrosion and separation difficulties in the fractionation zone, its condenser, and the chlorinator. Moreover, the crude ethylene dichloride obtained from the oxychlorination of ethylene, even after preliminary purification, often contains significant amounts of trichloroethylene. This trichloroethylene cannot be removed easily by fractional distillation, and may act as a reaction inhibitor when the ethylene dichloride product is later dehydrochlorinated. The oxychlorination effluent contains minor amounts of chloral, i.e., trichloroethanol, which pose additional separation problems. Again, the residual ethylene dichloride supplied to the distillation column from the pyrolysis system usually contains small amounts of chloroprene, i.e., 2-chloro-1,3-butadiene. Unless eliminated prior to entry into the fractionation zone, the chloroprene tends to polymerize and foul the column and condenser.

SUMMARY OF THE INVENTION

The present invention overcomes these objections by providing a method wherein ethylene and chlorine are reacted in a liquid reaction medium in the presence of a catalyst at a temperature of from about 80° C. to about 140° C. to produce crude ethylene dichloride, the crude ethylene dichloride produced is vaporized from the liquid medium by the heat of reaction and passed to a fractionation zone to which is also fed an ethylene dichloride-containing stream from an ethylene dichloride pyrolysis zone, the crude ethylene dichloride and the ethylene dichloride-containing stream are fractionated by the heat of reaction to produce a purer ethylene dichloride product, while concomitantly a partially purified, neutralized, and dried ethylene dichloride obtained from an oxychlorination effluent is fed to the liquid medium. In a preferred form, the invention comprises a method for producing ethylene dichloride comprising contacting ethylene and chlorine in a liquid reaction medium in the presence of a catalyst at a temperature of from about 80° C. to about 140° C. to produce crude ethylene dichloride, vaporizing the crude ethylene dichloride from the liquid reaction medium by the heat of reaction of the chlorine and ethylene, and passing the crude ethylene dichloride produced to a fractionation zone to which is also fed an ethylene dichloride-containing stream from an ethylene dichloride pyrolysis zone, fractionating the crude ethylene dichloride and the ethylene dichloride-containing stream utilizing the heat generated by the reaction of chlorine and ethylene to produce a purer ethylene dichloride product stream, while concomitantly feeding impure, or partially purified, neutralized, and dried ethylene dichloride obtained from an ethylene oxychlorination effluent to the liquid reaction medium the chlorine and ethylene are contacted, and utilizing the heat generated by the reaction of the chlorine and ethylene to vaporize the fractionate at least a portion of the crude ethylene dichloride obtained from the oxychlorination effluent. In its most preferred form, the invention provides for the chlorination of the ethylene dichloride-containing stream, prior to its entry into the fractionation zone, to chlorinate impurities, such as chloroprene, to heavier boiling impurities which may be removed in the fractionation zone.

DETAILED DESCRIPTION OF THE INVENTION

In order to describe the invention in greater detail, reference is made to the accompanying drawing. Ethylene and chlorine are introduced as gases via lines 1 and 2 into reactor 3, which contains a liquid medium containing ethylene dichloride, and a catalyst, e.g., ferric chloride. The chlorine and ethylene need not be pure. The chlorine, for example, may contain from 1 to 5 percent air, small amounts of hydrogen, as well as other components. Similarly, the ethylene may, and often does, contain minor amounts of other materials. The chlorine may be introduced as a liquid, wholly or partially, if desired. The chlorine and ethylene react in the liquid medium to form ethylene dichloride, and the ethylene dichloride is vaporized by the heat of reaction. The vaporized ethylene dichloride passes through line 4 to fractionation zone or column 5, wherein the heat generated by the reaction between chlorine and ethylene is utilized to fractionate the vaporized ethylene dichloride and produce a purified ethylene dichloride product. The ethylene dichloride may be taken off as a liquid or as a vapor, by techniques known to those skilled in the art, although the drawing indicates removal through line 6 as a liquid. Light ends, such as air, HCl, $H_2$, $Cl_2$ and minor amounts of miscellaneous chlorinated hydrocarbons, as well as some ethylene dichloride, are removed as overhead from fractionation zone 5 through line 7, cooled in exchanger 8, and passed through line 9 to collector-separator 10. In separator 10 the ethylene dichloride is largely separated from the other materials, and a non-condensable stream containing light-ends is removed to further recovery or waste through line 11. A portion or all of the cooled ethylene dichloride collected in unit 10 from the light-ends overhead is returned to fractionation zone 5 via line 12 to provide reflux, and some may be recovered, if desirable. Liquid collecting in the bottom of fractionation zone 5 is returned to reactor 3 via line 13, preferably to a point below the surface of the liquid reaction medium.

Fractionation zone 5 is also supplied with an ethylene dichloride-containing stream through line 14 from ethylene dichloride pyrolysis zone 15. More particularly, ethylene dichloride, e.g., that obtained from product line 6, is dehydrochlorinated or "cracked" in zone 15, under conditions and procedures known to those skilled in the art, to produce, after separation, crude vinyl chloride and a stream containing uncracked ethylene dichloride. The particular process employed in "cracking" the ethylene dichloride forms no part of the present invention, and any suitable procedure may be employed, as long as a stream containing residual or uncracked ethylene dichloride is characteristic of the process. In general, such streams will contain from about 90 mol percent to about 99.8 mol percent ethylene dichloride, the balance being random amounts of heavier chlorinated hydrocarbons, trichloroethylene, 1,1-dichloroethane, and other miscellaneous materials. Again, in most such processes, the ethylene dichloride-containing stream often contains significant minor amounts of chloroprene, for example, from 0.01 mol percent to about 0.08 mol percent chloroprene. This chloroprene tends to polymerize further along in the process. According to the invention, the ethylene dichloride-containing stream may be chlorinated in pipe or line 16, or, as shown, in chlorinator 17. The stream is chlorinated under appropriate conditions to convert the chloroprene in the stream to heavy-boiling chlorinated compounds. Any conventional method of chlorinating the chloroprene may be employed, so long as the method chosen does not significantly affect the other desired components in the stream or introduce other undesirable impurities. Some of the trichloroethylene in the stream may be chlorinated to higher-boiling materials, which is much to be desired.

More particularly, the stream may be chlorinated, using chlorine as the chlorinating agent, at a temperature of from about 0° C. to about 165° C., preferably at a temperature of from about 0° C. to about 120° C. The chlorine may be supplied at mol ratios of from about 0.7 mol of chlorine to about 3.0 mols of chlorine per mol of chloroprene present. A mol ratio of from about 1.0 mol of chlorine to about 2.5 mols of chlorine per mol of chloroprene is preferred. Catalysts may be added, although this is not normally necessary. The particular catalyst chosen is within the knowledge of the art, and forms no part of the present invention. Atmospheric, sub-atmospheric, or super atmospheric pressures may be employed. After the chlorination of the chloroprene in the stream, the stream is then passed via line 14 to fractionation zone 5 wherein the heavy-boiling impurities are easily removed. The heat of reaction of the chlorine and ethylene in reactor 3 is sufficient to accomplish the fractionation of this added stream, as well as of the vaporized crude ethylene dichloride produced by the reaction. If desired, fractionation zone 5 may contain a reboiler (not shown) for startup purposes and flexibility.

Concomitantly, an impure or partially purified, neutralized, and dried ethylene dichloride is introduced from an oxychlorination zone into the chlorinator 3 through line 18. More particularly, ethylene, oxygen (e.g., as air), and HCl, are contacted in zone 19 in the presence of a catalyst under appropriate conditions, known to those skilled in the art, to produce an effluent containing, inter alia, ethylene dichloride, HCl, ethylene, oxygen, $N_2$, small amounts of oxygenated compounds, and other chlorinated hydrocarbons and materials. The particular oxychlorination procedure used is not critical, and any conventional oxychlorination process may be employed. For example, the oxychlorination procedure used in Belgian Pat. No. 718,777 may be employed. Temperatures may range, for example, from about 180° C. to about 400° C., a range of from about 200° C. to about 375° C. being preferred. Pressures may be atmospheric or greater, and will normally range from about 1 atmosphere to about 50 atmospheres. Pressures of from 1 to about 30 atmospheres are preferred. Those catalysts normally used in oxychlorination procedures may be employed, the preferred catalysts being those containing cupric chloride.

The effluent from the oxychlorination zone is passed through line 20 to a variety of treatment procedures, including cooling or quench zone 21 and neutralization zone 22. In cooling zone 21, the oxychlorination effluent (e.g., at a temperature of from about 180° C. to about 400° C.) is cooled to yield a liquid mixture comprising impure ethylene dichloride, water, and HCl. The temperature of the effluent is lowered in the cooling zone to a range of from about 0° C. to about 80° C., and preferably will be from about 10° C. to about 50° C. After separation of at least the bulk of the water and HCl, the crude ethylene dichloride is then passed to zone 22 where it is contacted with a base, normally an inorganic base, such as an alkali metal or alkaline earth metal hydroxide, carbonate, or bicarbonate. Suitable basic materials include the hydroxides, carbonates, and bicarbonates of sodium, potassium, lithium, and calcium. The basic material neutralizes the residual HCl present in the effluent, and reacts with chloral to effect removal thereof. Sodium hydroxide, as a dilute caustic solution, is the preferred neutralizing and chloral removing agent. The basic material, e.g., NaOH, is preferably supplied in the form of a caustic solution containing from 1 percent to 20 percent by weight caustic, with a solution of from 2 percent to 10 percent by weight being preferred. The caustic and water soluble reaction products are easily separated from the crude effluent by phase separation.

The cooled, neutralized effluent is then forwarded to an azeotropic drying zone 23, and then to a light-ends removal zone 24, or a combination light-ends removal/drying column (not shown) may be employed. Where a separate drying zone is employed, the drying may be accomplished by fractionation, as indicated, according to well established principles, or may be accomplished by drying agents, such as $CaCl_2$, or molecular sieves. In any event, the effluent (crude ethylene dichloride) fed to chlorinator 3 should contain quite limited amounts of water, e.g., not more than about 10 to 30 parts per million. Although greater amounts may be present, the problems indicated, i.e., corrosion, etc., begin to appear in direct relation to the amount of water present. Accordingly, as little water as possible should be present in the crude ethylene dichloride supplied to the chlorinator 3.

The now neutral, dried, and partially purified oxychlorination effluent is forwarded from zone 24 via line 18 to chlorinator 3. The effluent is preferably introduced as a liquid into chlorinator 3 below the surface of the liquid reaction medium, although it may be admitted as a gas, if desired. The temperature and pressure will depend on a variety of factors, such as the temperature and pressure of column 24. If desired, the partially purified effluent may be heat-exchanged before introduction into chlorinator 3. The temperature of the effluent introduced will preferably be from about 90° C. to about 130° C., although, as indicated, wide variations may be employed. In chlorinator 3 the ethylene dichloride in the oxychlorination effluent is vaporized by the heat of reaction of the chlorine and ethylene, and is passed together with the ethylene dichloride obtained from the chlorination reaction to fractionation zone 5 via line 4. As indicated, product ethylene dichloride, including the now fractionated oxychlorination effluent ethylene dichloride, may be removed through line 6. High boiling impurities from the direct chlorination reaction, as well as those from the ethylene dichloride-containing stream from the ethylene dichloride pyrolysis zone and the impure oxychlorination effluent, are removed eventually from the bottom of chlorinator 3 through line 5.

Not all of the oxychlorination effluent need be sent to chlorinator 3. For example, a portion may be sent to fractionation column 5. However, as indicated, problems associated with trichloroethylene buildup will be magnified in proportion to the amount sent to the column. The oxychlorination effluent may contain added crude ethylene dichloride from other sources in minor amounts, e.g., up to 10 mol percent and even 20 mol percent. For example, minor amounts of crude ethylene dichloride from other sources may be added to the oxychlorination effluent in or prior to the caustic treatment step.

The temperatures at which the chlorination reaction is carried out in chlorinator 3 include those temperatures at which a portion of the liquid medium, into which the ethylene and chlorine are introduced, will vaporize under the pressure conditions employed. Thus, where ethylene dichloride is the desired product, the reaction of ethylene and chlorine is carried out in a liquid medium maintained at a temperature of from about 80° C. to about 140° C., so that the ethylene dichloride, which normally boils at about 83.5° C., will vaporize readily from the system. Temperatures from about 95° C. to about 130° C. are preferred. In actuality, the temperature will vary in the liquid medium from the top of chlorinator 3, (e.g., the temperature might be about 90° C.) to the bottom of the reactor, where the temperature will be somewhat higher due to static pressure. Again, as indicated, the actual temperatures employed will depend on the composition of the medium, as well as the pressures utilized.

With respect to pressures employed, the reaction in chlorinator 3 may be effected at any suitable pressure, so long as a portion of the liquid medium, within which the olefin and chlorine react to produce additional quantities of the medium, will vaporize as a result of the exothermic heat of reaction. For example, pressures of from about 0.5 atmosphere to about 4 or 5 atmospheres may be employed, and pressures of from 0.8 atmosphere to about 2.0 atmospheres are preferred.

The concentrations or ratios of reactants supplied to the liquid reaction medium may be varied to considerable extent. Preferably, the reactants are supplied in such proportions that there is a slight excess of ethylene over and above the stoichiometric amount required to react with the chlorine. A preferred ratio is from about 1.01 mols to about 1.10 mols of ethylene per mol of chlorine. However, a small excess of chlorine may be employed.

The liquid phase reaction of ethylene and chlorine is generally conducted in the presence of a catalyst. In the process of the invention, any of the well known catalysts generally associated with this reaction may be employed. For example, metal chlorides, such as ferric chloride, antimony chloride, and copper chloride, may be used. Ferric chloride is preferred. The specific catalyst employed is a matter of choice, and constitutes no part of the invention.

Any suitable composition of reaction liquids may be employed, provided the medium can be operated under suitable conditions, as outlined above, to vaporize a portion of the ethylene dichloride, a part thereof, or that formed by the chlorination reaction. Normally, the liquid reaction medium will comprise a significant amount of ethylene dichloride, although other liquids may be present, even in major amounts. For example, the liquid reaction medium may contain large amounts, e.g., up to 50 percent or 60 percent or greater, of 1,1,2-trichloroethane. The liquid reaction medium will generally comprise largely chlorinated hydrocarbons, including ethylene dichloride, 1,1,2-trichloroethane, heavy boiling chlorinated compounds, etc., and various amounts of chlorinated hydrocarbon impurities, their reaction products, oxygenated impurities, the impurities from the oxychlorination effluent, and any materials refluxing from the fractionation column.

Although the drawing illustrates the use of a separate fractionation zone for the vapors from the ethylene chlorinator, those skilled in the art will appreciate that a system in which the fractionation zone or column is made an integral part of the reactor falls within the scope of the invention.

What is claimed is:

1. A method for producing ethylene dichloride comprising contacting ethylene and chlorine in a liquid reaction medium comprising ethylene dichloride in the presence of a catalyst at a temperature of from about 80° C. to about 140° C. to produce crude ethylene dichloride, while concomitantly feeding impure, neutralized, and dried ethylene dichloride from which chloral has been removed and which is obtained from an ethylene oxychlorination effluent, to the liquid reaction medium; vaporizing the crude ethylene dichloride and said impure ethylene dichloride together from the reaction medium by the heat of reaction of the chlorine and ethylene; passing the vaporized ethylene dichloride to a fractionation zone to which is also fed an ethylene dichloride-containing stream from an ethylene dichloride pyrolysis zone; fractionating the vaporized ethylene dichloride and the ethylene dichloride-containing stream, utilizing the heat of reaction of the chlorine and ethylene, to produce a purer ethylene dichloride product stream.

2. The process of claim 1, wherein the ethylene dichloride-containing stream from an ethylene dichloride pyrolysis zone is chlorinated prior to the stream's entry into the fractionation zone to chlorinate undesired impurities to heavier-boiling impurities.

3. A method for producing ethylene dichloride comprising contacting ethylene and chlorine in a liquid reaction medium comprising ethylene dichloride in the presence of a catalyst at a temperature of from about 80° C. to about 140° C. to produce crude ethylene dichloride, while concomitantly contacting ethylene, hydrogen chloride, and an oxygen-containing gas in the presence of an oxychlorination catalyst at a temperature of from about 180° C. to about 400° C. to produce a crude oxychlorination effluent;

cooling the crude oxychlorination effluent to condense the bulk of the ethylene dichloride and water in the effluent and form a crude condensed oxychlorination effluent, and separating the bulk of the water from the crude effluent;

neutralizing the condensed oxychlorination effluent and removing chloral therefrom;

removing low-boiling impurities and water from the crude neutralized, condensed effluent to form a partially purified, neutralized, and dried oxychlorination effluent;

feeding the partially-purified, neutralized, and dried oxychlorination effluent to the liquid reaction medium; vaporizing the crude ethylene dichloride and said partially-purified ethylene dichloride together from the reaction medium by utilizing the heat of reaction of the chlorine and ethylene; passing the vaporized ethylene dichloride to a fractionation zone to which is also fed an ethylene dichloride-containing stream from an ethylene dichloride pyrolysis zone; fractionating the vaporized ethylene dichloride and the ethylene dichloride-containing stream, utilizing the heat of reaction of the chlorine and ethylene, to produce a purer ethylene dichloride product stream.

4. The process of claim 3, wherein the ethylene dichloride-containing stream from an ethylene dichloride pyrolysis zone is chlorinated prior to the stream's entry into the fractionation zone to chlorinate undesired impurities to heavier-boiling impurities.

* * * * *